United States Patent [19]

Mushika

[11] Patent Number: 4,655,748

[45] Date of Patent: Apr. 7, 1987

[54] CANNULA FOR INFUSION OF FLUID

[75] Inventor: Sadahiko Mushika, Tokyo, Japan

[73] Assignee: Aisin Seiki Kabushikikaisha, Aichi, Japan

[21] Appl. No.: 772,534

[22] Filed: Sep. 4, 1985

[30] Foreign Application Priority Data

Sep. 4, 1984 [JP] Japan .................. 59-185051

[51] Int. Cl.$^4$ .................................. A61M 29/00
[52] U.S. Cl. ..................... 604/96; 128/1 D; 128/344; 128/348.1
[58] Field of Search ........... 128/1 D, 325, 344, 348.1; 604/96, 99

[56] References Cited

U.S. PATENT DOCUMENTS

| 3,585,983 | 6/1971 | Kantrowitz et al. | 128/344 |
|---|---|---|---|
| 3,592,183 | 7/1971 | Watkins et al. | 128/1 D |
| 3,592,184 | 7/1971 | Watkins et al. | 128/1 D |
| 4,261,339 | 4/1981 | Hanson et al. | 128/1 D |
| 4,276,874 | 7/1981 | Wolvek et al. | 128/1 D |
| 4,292,974 | 10/1981 | Fogarty | 128/344 |
| 4,311,133 | 1/1982 | Robinson | 128/1 D |
| 4,338,942 | 7/1982 | Fogarty | 128/344 |
| 4,362,150 | 12/1982 | Lombardi et al. | |
| 4,402,307 | 9/1983 | Hanson et al. | 128/344 |
| 4,403,612 | 9/1983 | Fogarty | 128/344 |
| 4,407,271 | 10/1983 | Schiff | 128/1 D |
| 4,448,195 | 5/1984 | Le Veen et al. | 128/344 |
| 4,467,790 | 8/1984 | Schiff | 128/344 |
| 4,522,195 | 6/1985 | Schiff | 128/1 D |
| 4,531,512 | 7/1985 | Wolvek et al. | 128/325 |
| 4,545,390 | 10/1985 | Leavy | 604/95 |
| 4,552,127 | 11/1985 | Schiff | 128/1 D |

FOREIGN PATENT DOCUMENTS 0995751 2/1983 U.S.S.R. ................. 128/344

Primary Examiner—C. Fred Rosenbaum
Assistant Examiner—Jerome R. Smith, Jr.
Attorney, Agent, or Firm—Sughrue, Mion, Zinn, Macpeak & Seas

[57] ABSTRACT

A cannula for infusion of blood into a blood vessel includes a flexible membrane member which is secured to the leading end of a blood admitting pipe. An end insert is secured to the leading end of the flexible membrane member, and a core member is fixedly connected to the end insert. A fluid passage opening is formed in either the end insert or the flexible membrane member so as to permit the discharge of a blood which is infused into the flexible membrane member from an external source through the blood admitting pipe. The flexible membrane member may be folded and wrapped around the core member when the cannula is to be inserted into a blood vessel. As the blood begins to be fed into the pipe, the flexible membrane member is caused to be inflated, and blood flows into a blood vessel from the flexible membrane member.

7 Claims, 6 Drawing Figures

CANNULA FOR INFUSION OF FLUID

BACKGROUND OF THE INVENTION

The invention relates to an apparatus for infusion of fluid into a physical body, in particular, cannula for infusion of body fluid into a flow path of a living body such as arteria femoralis as when conducting an extracorporeal circulation of body fluid, such as intracorporeal blood, in an artificial heart and lung, artificial kidney, auxiliary artificial heart or the like.

PRIOR ART

When conducting an extracorporeal circulation of blood of a living body through an artificial heart and lung, for example, the general process is as illustrated in FIG. 4 where a cannula 4 for admitting or infusing blood is inserted into arteria femoralis 2f while a cannula 5 for withdrawing blood is inserted into vena femoralis 3f, thus withdrawing the blood from the vena femoralis 3f through the cannula 5 to be fed into an artificial heart and lung 6 where the blood is processed, whereupon the processed blood is admitted or fed into the arteria femoralis 2f through the cannula 4. The diameter of the leading end of the cannula 4 cannot be reduced since then the tube resistance increases. Accordingly, the admitting cannula 4 is inserted by a surgical cutdown of the blood vessel 2f, because it cannot be inserted into the blood vessel of the arteria hypodermically. The need for a surgical cutdown means that the extracorporeal circulation can only be conducted at a particular installation such as a hospital which is provided with facilities for surgical operations. Thus, there arises a problem that an extracorporeal circulation for emergency purpose can hardly be conducted until the time a patient is transferred to a given installation.

SUMMARY OF THE INVENTION

It is an object of the invention to provide a cannula for infusion of fluid such as may be used to admit blood, which can be easily inserted into a living body by a hypodermic process and which exhibits a reduced tube resistance.

In accordance with the invention, there is provided a cannula for infusion of fluid comprising a fluid infusion pipe, a flexible membrane member having its one open end fixedly connected to the leading end of the pipe and having a diameter greater than the diameter of the pipe, an end insert which is integral with the other open end of the flexible membrane member, a flexible core member having its one end joined to the end insert and extending through the flexible membrane member into the pipe, and a fluid passage opening formed in the end insert and/or the flexible membrane member and communicating with the internal space of the pipe through an internal space within the flexible membrane member. With this arrangement, the end insert may be rotated to cause the flexible membrane member to be wrapped around the flexible core member to provide "twisted strands", in a similar manner as an open umbrella is closed or folded, thus providing a bendable wire which can be hypodermically inserted into a fluid duct, for example, into the arteria femoralis. By way of example, a piercer having an internal diameter which is slightly greater than the outer diameter of the "bendable wire" may be pierced into the arteria femoralis, and the "bendable wire" may be inserted thereinto, whereupon the piercer may be withdrawn. In this manner, the "bendable wire" can be inserted into the arteria femoralis. When a blood stream is fed through the pipe into the flexible membrane member of the "bendable wire", the balloon is inflated, thus closing the blood vessel and allowing the admitted blood stream to be delivered from the flexible membrane member into the arteria.

Other objects and features of the invention will become apparent from the following description of embodiments thereof with reference to the drawings.

BRIEF DESCRIPTION OF THE DRAWINGS

FIG. 1b is an enlarged perspective view of one end of a core member shown in FIG. 1a;

DESCRIPTION OF PREFERRED EMBODIMENTS

Figure 1A:
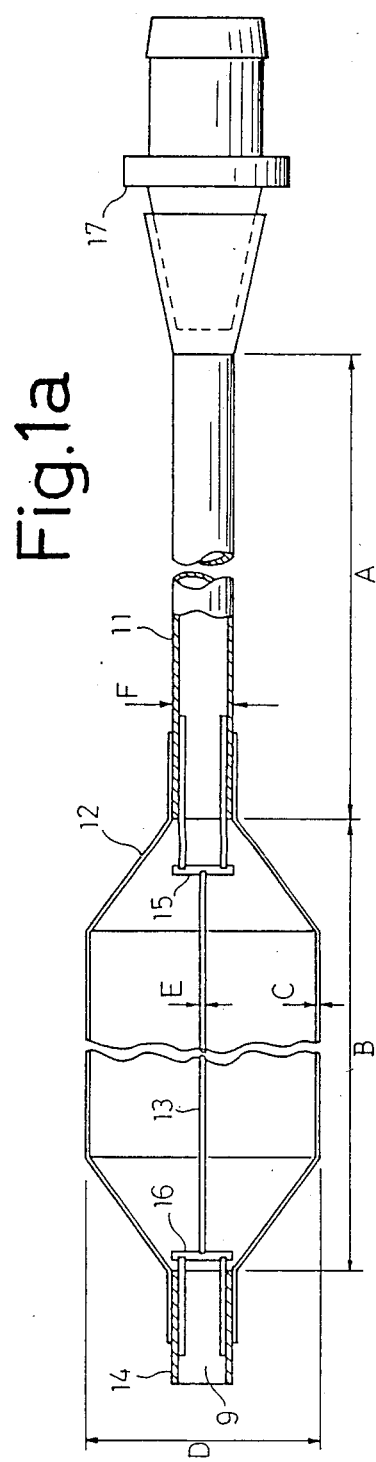
FIG. 1a is a side elevation, partly cut away and in longitudinal section, of an embodiment of the invention.
Figure 1B:
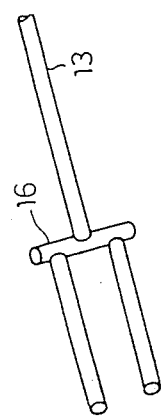

Referring to FIG. 1a, there is shown a cannula for admitting blood into the arteria according to a first embodiment of the invention. In FIG. 1a, the right-hand portion of the cannula is shown in elevation to show its appearance while its left-hand portion is shown in longitudinal section. A blood admitting pipe 11 has its one end expanded in the form of a funnel, where a connector 17 is fixedly attached for connection of a fluid tube leading to an instrument such as an artificial heart and lung. The blood admitting pipe 11 is formed of an antithrombic polyurethane material, and has its other end fixedly connected to one end of a flexible tube 12, which is also formed of an antithrombic polyurethane material. A cylindrical end insert 14, also formed of an antithrombic polyurethane material, is secured to the other end of the flexible tube 12. A core member 13 formed of stainless steel has its opposite ends 15, 16 branched into ][-configuration, as shown, which extend inwardly into the pipe 11 and the end insert 14, respectively. FIG. 1b shows one end of the core member 13 to an enlarged scale. Each end 15, 16 of the core member 13 extends into the pipe 11 and the end insert 14, respectively, but is not fixedly connected therewith and hence is rotatable and slidable with respect to the pipe 11 and the end insert 14, respectively.

Table 1 below indicates the dimensions of various parts of the cannula shown in FIG. 1a.

TABLE 1

| Designation | A | B | C | D | E | F |
|---|---|---|---|---|---|---|
| Dimension (mm) | 150 | 300 | 0.1 or less | 10 | 0.2 to 0.3 | 4 |

Figure 1C:
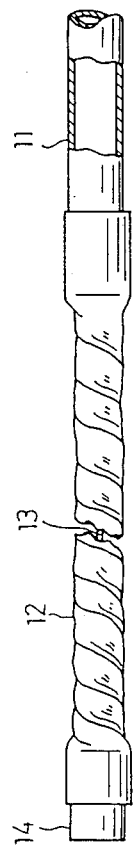
FIG. 1c is a side elevation of a flexible tube shown in FIG. 1a which is in its folded configuration.

The flexible tube 12 is constructed by a thin membrane so that it can be folded into the configuration of "twisted strands" as shown in FIG. 1c of a diameter which is less than the external diameter of the pipe 11 when the end insert 14 is rotated about the core member 13. It will be understood that the flexible tube can also be folded into a string form of a diameter less than the outer diameter of the pipe 11 when it is wrapped around the core member 13. When inserting the cannula into the arteria femoralis, a piercer having an internal diameter which is slightly greater than the outer diameter (4 mm) of the pipe 11 is initially hypodermically pierced into the arteria femoralis, and then the cannula having a reduced dimension as illustrated in FIG. 1c is then inserted through the interior of the piercer into the arteria, with the end insert 14 located at the front. Subsequently, the piercer is removed from the arteria. When a stream of the blood to be admitted is fed into the pipe, the stream flows along the core member 13 to reach the end insert 14, and thence into the arteria femoralis. The pressure of the admitting blood and the restoring force of the flexible tube cause the tube to be unfolded to be inflated, thus reducing the tube or channel resistance from the connector 17 to the end insert 14 or the entire cannula.

Figure 2:
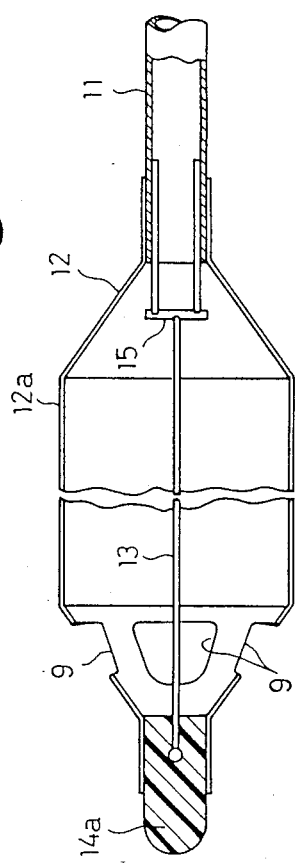
FIG. 2 is a longitudinal section of another embodiment of the invention.

FIG. 2 shows a second embodiment of the invention in which an end insert 14a is constructed as a solid member in the form of a bullet which facilitates its insertion into the arteria femoralis. One end of the core member 13 is embedded in and secured to the end insert 14a. Fluid passage openings 9 are formed in a flexible tube 12a toward the end insert 14a. In other respects, the arrangement is similar to the embodiment of FIG. 1a, and the manner of use remains the same as in FIG. 1a.

Figure 3:
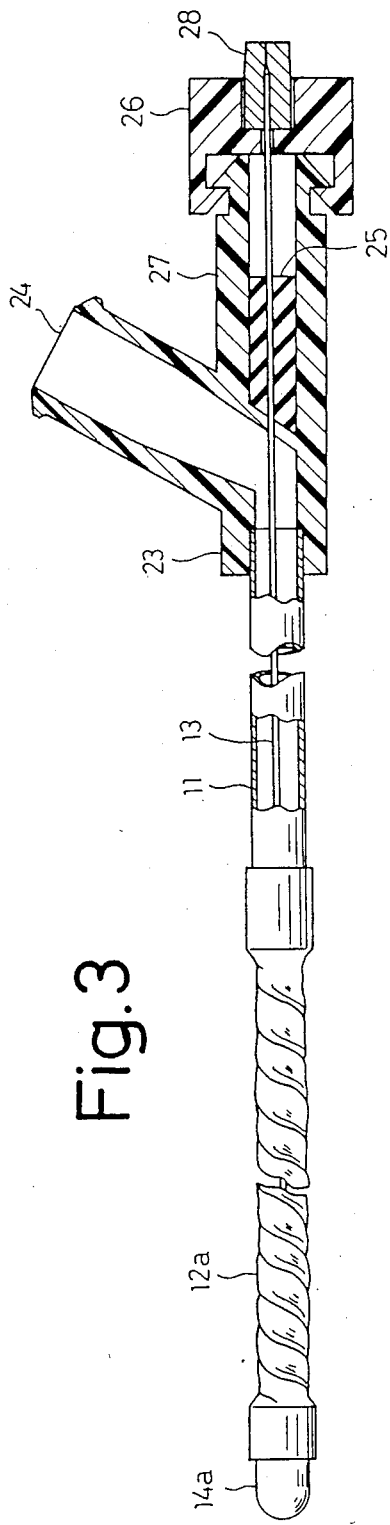
FIG. 3 is a side elevation, partly in longitudinal section, of a further embodiment of the invention.
Figure 4:
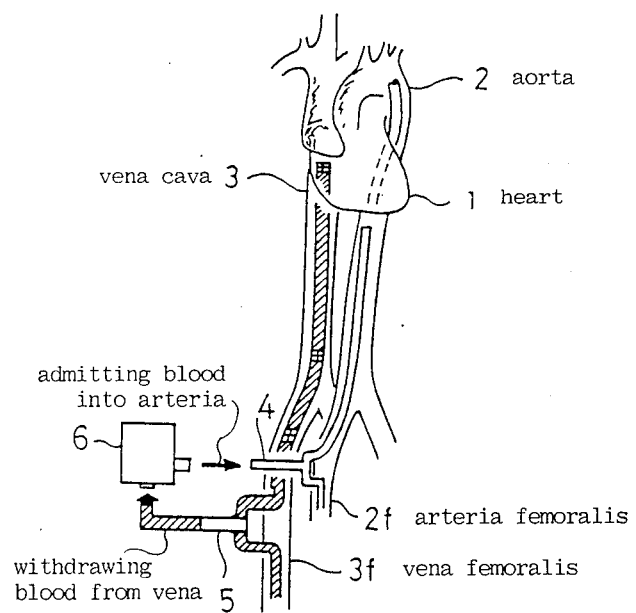
FIG. 4 is an illustration of the essential construction of an extracorporeal circulation system which includes an artificial heart and lung, a blood withdrawing cannula, a blood admitting cannula and blood vessels of a human body.

FIG. 3 shows a further embodiment of the invention. The construction of an end member 14a and a flexible tube 12a remains the same as shown in FIG. 2. However, the other end of the core member 13 extends through the internal surface of the pipe 11 and also extends through a connector 23. The connector 23 includes a port 24 which receives a stream of blood to be admitted and another port 27 through which the core member 13 extends, and thus the connector is substantially Y-shaped. At the port 27, the core member 23 extends through an elastic member 25 which provides a seal against the blood stream, and thus is located outside the port 27 where a locking piece 28 having a rectangular configuration is secured thereto by means of a force fit. An operating member 26 is rotatably fitted around the end of the port 27, and is formed with a rectangular opening in which the locking piece 28 is received. When the connector 23 is held stationary and the operating member 26 is rotated, the core member 23 is twisted, whereby the end insert 14a is rotated, thus folding the flexible tube 12a into the configuration of "twisted strands" as shown in FIG. 3. After the end insert 14a and the flexible tube 12a which is then in the form of "twisted strands" as shown in FIG. 3 are inserted into the arteria, the operating member 26 may be rotated in the opposite direction from the direction in which it is rotated when forming the "twisted strands", whereby the flexible tube 12a is unfolded and is easily inflated. A stream of admitting blood causes the tube to be inflated.

As described, the cannula for infusion of fluid according to the invention can be easily inserted into a fluid path such as the arteria femoralis by a hypodermic process, with a reduced tube resistance after the insertion.

While several preferred embodiments of the invention have been illustrated and described above, it should be understood that a variety of changes, modifications and substitutions will readily occur to one skilled in the art without departing from the spirit and the scope of the invention as defined by the appended claims.

What is claimed is:

1. A cannula for the infusion of fluid comprising a pipe having a leading end adapted to be inserted into a blood vessel within a body and a trailing end adapted to be connected to blood supply means exteriorly of the body for supplying blood into the blood vessel, a flexible, expandable, tubular membrane member having an opening at each end and a central portion adapted to have a greater diameter than the diameter of said pipe upon expansion, one end of said flexible membrane member being secured to the leading end of said pipe, an end insert secured in the other end of said flexible membrane member, a flexible core member having one end joined to said end insert and extending through said flexible membrane member into said pipe and a fluid passage opening formed in at least one of said end insert and said flexible membrane member for providing communication between the interior of said flexible membrane member and the interior of the blood vessel.

2. A cannula as set forth in claim 1 wherein said flexible membrane member is in the form of a tubular expandable bag having opposite open ends and wherein said insert is formed with a fluid passage opening for providing communication between the interior of the flexible membrane member and the interior of the blood vessel.

3. A cannula as set forth in claim 1 wherein said end inset is a solid member which closes the end opening of the flexible membrane member in which the end insert is secured and said flexible membrane member is provided with at least one fluid passage opening adjacent said end insert for providing communication between the interior of the flexible membrane member and the interior of the blood vessel.

4. A cannula as set forth in claim 2 wherein said flexible core member has one end secured to said end insert and the other end secured to said pipe.

5. A cannula as set forth in claim 3 wherein said flexible core member has one end secured to said end insert and the other end secured to said pipe.

6. A cannula as set forth in claim 4 wherein said flexible core member has one end secured to said end insert while the other end thereof extends outwardly of the trailing end of said pipe and further comprising rotation means secured to said other end of said flexible core member for rotating said flexible core member and said end insert.

7. A cannula as set forth in claim 5 wherein said flexible core member has one end secured to said end insert while the other end thereof extends outwardly of the trailing end of said pipe and further comprising rotation means secured to said other end of said flexible core member for rotating said flexible core member and said end insert.

* * * * *